United States Patent

Meals

[11] Patent Number: 5,147,286
[45] Date of Patent: Sep. 15, 1992

[54] HIP ABDUCTION DEVICE

[75] Inventor: Roy A. Meals, Los Angeles, Calif.
[73] Assignee: Bissell Healthcare Corporation, Grand Rapids, Mich.
[21] Appl. No.: 573,679
[22] Filed: Aug. 27, 1990
[51] Int. Cl.⁵ .............................. A61F 5/00
[52] U.S. Cl. ................................ 602/24
[58] Field of Search .......... 128/87 C, 88, 882, 80 R, 128/80 A

[56] References Cited

U.S. PATENT DOCUMENTS

| | | |
|---|---|---|
| 1,768,770 | 7/1930 | Kettelkamp . |
| 2,492,920 | 12/1949 | Koster .................. 128/88 |
| 2,815,021 | 12/1957 | Freeman ............... 128/80 A |
| 2,832,334 | 4/1958 | Whitelaw . |
| 3,256,880 | 6/1966 | Caypinar . |
| 3,260,259 | 7/1966 | Connelly ............... 128/87 C |
| 3,472,224 | 10/1969 | Ewerwahn . |
| 4,263,901 | 4/1981 | Nichols ................. 128/80 A |
| 4,543,948 | 10/1985 | Phillips et al. ......... 128/80 A |
| 4,550,722 | 11/1985 | Kurtz et al. ........... 128/80 A |
| 4,607,629 | 8/1986 | Lerman ................. 128/80 A |
| 4,807,609 | 2/1989 | Meals . |

FOREIGN PATENT DOCUMENTS 1343850 1/1974 United Kingdom ............ 128/80 A

OTHER PUBLICATIONS

Healthcare Catalog, Fred Sammons Inc., 1990, p. B32.
Journal of Bone & Joint Surgery, Advertisement for Richards Pehr Abduction Splint, p. 81, vol. 47A, No. 2, Mar. 1965.

Primary Examiner—Robert A. Hafer
Assistant Examiner—Kevin G. Rooney
Attorney, Agent, or Firm—Price, Heneveld, Cooper, DeWitt & Litton

[57] ABSTRACT

The present invention is a collapsible hip abduction device for properly positioning a patient's lower limbs. The device has a peripheral wire frame and a removable fabric covering. Securing straps are also provided. The device can easily be sanitized for use by a subsequent patient.

16 Claims, 2 Drawing Sheets

HIP ABDUCTION DEVICE

BACKGROUND OF THE INVENTION

The present invention relates to medical splinting generally and hip abduction devices specifically.

Patients recovering from hip surgery, strokes or other illnesses causing muscle imbalance must guard against and prevent hip adduction which occurs when the lower limbs are crossed or the like. Rather it is preferred during the normal recovery period, up to two weeks, that when lying horizontal, sleeping or otherwise immobilized, the patient's lower limbs are secured in a state of abduction. A recognized angle of abduction for each hip is approximately 30° each, giving an included angle of approximately 60° between the two lower limbs. The angle of abduction is measured from the center line between the lower limbs when they are aligned with each other which is the zero abduction angle.

Prior hip abduction devices have basically consisted of a wedge shaped foam pillow secured between the lower limbs. Such devices are bulky to handle and store. Such devices also restrict the circulation of air along the patients skin where the device is used, causing irritation and general discomfort. Further, the wedge shaped foam devices are difficult to clean or sanitize for prolonged use or use by subsequent patients.

SUMMARY OF THE INVENTION

The collapsible hip abductor of the present invention addresses the deficiencies of the prior hip abductor devices and provides a collapsible device having two wire frame support arms which are releasably connected at one end and have a removable fabric covering.

In one aspect of the invention, the use of a removable fabric covering over a stainless steel wire frame enhances the ability to clean and sanitize the device. The fabric also enhances free air circulation to the body portion engaged thereby. The configuration of the wire frame is such that no body portion need impact the wire frame itself. In another aspect of the invention, the assembled device does not have the bulk of the prior devices. The two support arms can be disconnected from each other to further minimize the bulk of the present device and enhance its compact storage. The preferred embodiment constitutes about one-tenth the bulk of the prior art referenced when in its collapsed state.

These and other objects, advantages and features of the present invention will become apparent upon review of the following specification in conjunction with the drawings.

DESCRIPTION OF THE PREFERRED EMBODIMENT

Figure 1:
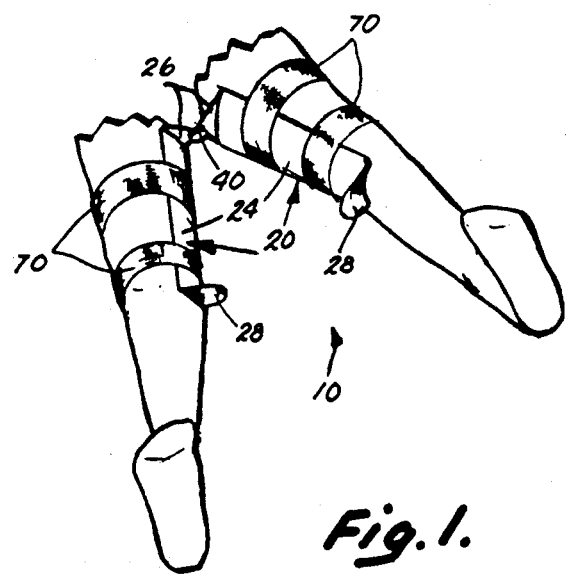
FIG. 1 is a perspective view of the invention as used by a patient.
Figure 2:
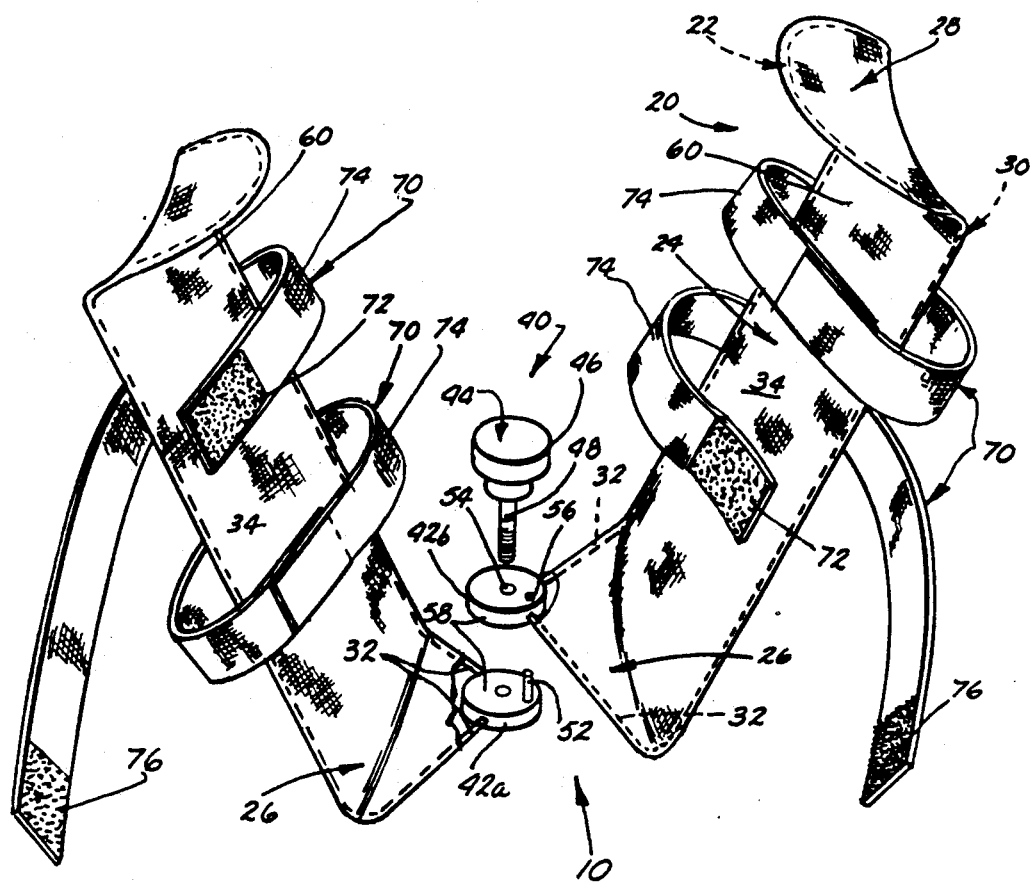
FIG. 2 is an exploded perspective view of the invention.
Figure 3:
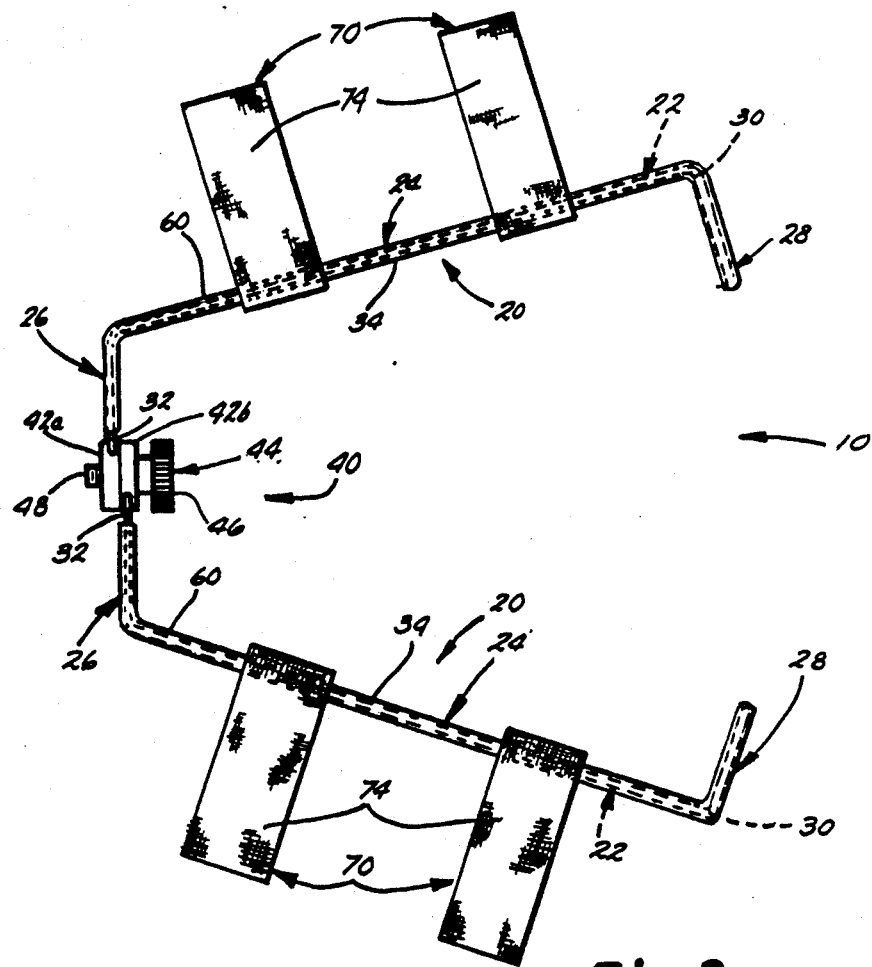
FIG. 3 is a top plan view of the invention.

In the preferred embodiment, the collapsible hip abductor 10 of the present invention includes two support arms 20 releasably connected to each other by an attachment device 40 (FIGS. 1, 2 and 3). The support arms 20 are covered with a flexible material 60 and are releasably fastened to a patient's legs by fastening straps 70 (FIG. 1).

Figure 4:
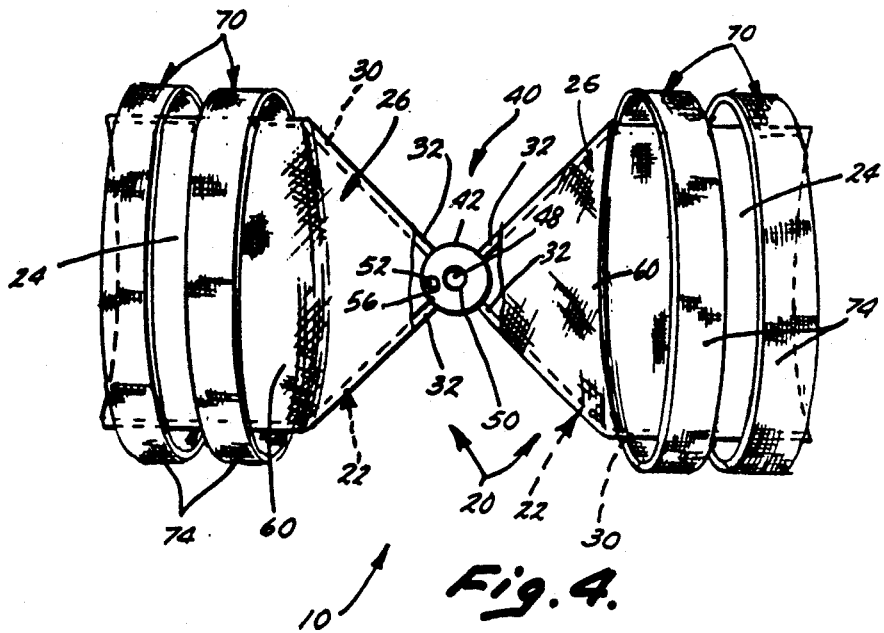
FIG. 4 is an end elevational view of the invention.

Each support arm 20 has a peripheral framework 22, preferably made from a continuous piece of stainless steel wire 30 (FIGS. 2, 3 and 4). The size of the wire 30 depends upon the specific duration of use of the hip abductor 10. If the hip abductor 10 is used during a post surgery recovery period or other circumstance requiring only a few weeks of treatment, a wire size of about 0.187 inch diameter is appropriate. However, an extended treatment period, such as would be required in the case of disease for example, will require a more durable device and an appropriately thicker wire size. Each arm 20 includes a generally planar mid portion 24 with a proximal flange 26 at one end and a distal flange 28 at the other end (FIG. 3).

Distal flange 28 projects generally perpendicularly from mid portion 24, roughly 80° in the preferred embodiment. The distal flange portion 28 is semi-circularly shaped, having a 3 inch radius in the preferred embodiment (FIG. 2). This configuration removes the wire from directly impacting the patient's body.

The proximal flange 26 is triangularly shaped and includes a disk 42 of attachment device 40. The two ends of stainless steel wire 30 are connected to disk 42 so that a 90° included angle is formed between the end portions 32 of wire 30 (FIG. 2). Proximal flange 26 projects to the same side of mid portion 24 as distal flange 28 and forms an included angle of 115° between the proximal flange 26 and mid portion 24 (FIG. 3).

Attachment device 40 includes two disks 42, each approximately 0.25 inch thick and cut from about 1.375 inch diameter aluminum rod in the preferred embodiment (FIGS. 2, 3 and 4). Attachment device 40 also includes a hand screw 44 for fastening the two disks 42 together. Hand screw 44 includes a handle 46 and a threaded shaft 48. Disc 42a includes a generally centered threaded aperture 50 for receiving threaded shaft 48 and an indexing pin 52 for indexing the alignment between disks 42 (FIG. 2). Disk 42b includes a generally centered aperture 54 which is preferable threaded for better stability, for receiving threaded shaft 48 and an indexing aperture 56 for receiving indexing pin 52.

Flexible material 60 is preferably a knit cotton blend as is commonly found in athletic socks and the like. Material 60 is fabricated in a sock-like fashion to form a fabric tube with one open end and one closed end. The resulting "sock" is simply slid over the peripheral framework 22 in a sock-like manner to assemble the "sock" to a support arm 20 (FIGS. 2 and 4). The "sock" breathes freely to allow air circulation to the body parts in contact therewith.

At least one, preferably two, fastening straps 70 are attached to each support arm 20. Each fastening strap 70 has one end 72 which is fitted with the loop portion of a hook and loop fastening fabric and which is attached to the inner surface 34 of support arm 20 (FIG. 2). Each strap 70 also has a back surface 74 which also has a loop type fabric for releasably receiving the hook portion of a hook and loop fastening fabric. The other end 76 of each strap 70 is fitted with the loop portion of the hook and loop fastening fabric so that each strap 70 can be wrapped around the users lower limb to fasten the arm 20 to the limb and the end 76 can be releasably connected to the end 72 or to the back surface 74 of strap 70 as is most appropriate for proper adjustment and fitment.

In use, support arms 20 are assembled together as shown in FIG. 2 by inserting threaded shaft 48 of hand screw 44 through aperture 54 of disk 42b and further, screwing threaded shaft 48 into threaded aperture 50 of disk 42a. Indexing pin 52 of disk 42a is aligned with indexing aperture 56 of disk 42b as the disks 42 are drawn together by the screw action of hand screw 44. This indexing function can be accomplished in numerous ways, such as contouring the surfaces 58 of disks 42 for complementary, abutting engagement (FIG. 2). However, for simplicity of use and minimal cost, the indexing pin 52 and indexing aperture 56 are preferred.

Having coupled support arms 20 together via attachment device 40, the hip abductor 10 is positioned between the patients lower limbs and secured with fastening straps 70 as shown in FIG. 1.

Collapsible hip abductor 10 can easily be cleaned and sanitized by removing the flexible material 60 from the peripheral framework 22 of each support arm 20 in a sock-like manner. Flexible material 60 with straps 70 attached can easily be laundered or replaced. The peripheral frame work 22 of support arms 20 and attachment device 40 can be sanitized using standard methods.

The above description is considered that of the preferred embodiment only. Modifications of the invention will occur to those who make or use the invention. Therefore, it is understood that the embodiment shown in the drawings and described above is merely for illustrative purposed and is not intended to limit the scope of the invention which is defined by the following claims as interpreted according to the principles of patent law.

I claim:

1. A collapsible hip abductor device comprising, in combination:

first and second support arms adapted to support and index the lower limb position of a patient to properly position the patient's hips and inhibit improper positioning, said first and second support arms being substantially similar in configuration, and each being formed of a peripheral frame work comprising a single continuous length of wire;

said peripheral wire frame work defining (1) a mid portion having two opposing side edges, a proximal end and a distal end, (2) a generally triangularly-shaped proximal end flange portion extending from said proximal end of said mid portion to an apex at an angle to said mid portion of approximately 115°; and a generally semi-circular shaped distal end flange portion projecting from said distal end of said mid portion, said proximal and distal end flange portions projecting to the same side of said mid portion;

a flexible material suspended within at least across said mid portion of said frame work, said flexible material providing a seat for the thigh region of each lower limb of the patient, said proximal and distal ends of said mid portion being open between said opposing side edges whereby a portion of a user's thigh can lie between said opposing side edges, causing said flexible material to contour to the shape of the user's thigh;

attachment means for securing said first and second arms together, comprising a first one of said support arms including a first cooperating attachment member secured to said apex of said proximal end flange of said first support arm;

the second of said support arms including a second cooperating attachment member secured to said apex of said proximal end flange of said second support arm, and said first and second cooperating members being adapted to releasably and directly interconnect for positioning said first and second support arms in a predetermined orientation defining an included angle between said first and second arms of approximately 50°; and said support arms further including releasable fastening means for attaching each support arm to the respective legs of the patient.

2. The collapsible hip abductor defined in claim 1 wherein said first cooperating member has a bottom surface, said second cooperating member has a top surface and said top and bottom surfaces are complementary so that said top surface is butted against said bottom surface to index the relative position of said first and second cooperating members.

3. The collapsible hip abductor defined in claim 2 wherein:

said top surface and said bottom surfaces of said respective cooperating members are generally planar;

said first cooperating member has a first aperture extending through said first cooperating member, said first aperture being generally perpendicular to said bottom surface;

said first cooperating member has a second aperture extending through said first cooperating member, said second aperture being generally perpendicular to said bottom surface;

said second cooperating member has a third aperture extending through said second cooperating member, said third aperture being aligned with said first aperture and being generally perpendicular to said top surface, at least one of said first and third apertures being threaded;

said second cooperating member has a fourth aperture extending through said second cooperating member, said fourth aperture being aligned with said second aperture and being generally perpendicular to said top surface;

said attachment means further includes a hand screw for engaging said first and third apertures to screw said first and second cooperating members together; and said attachment means further includes an indexing pin fastened in one of said second and fourth apertures and projecting therefrom for inserting through the other of said second and fourth apertures to rotationally position said first and second cooperating members relative to each other.

4. The collapsible hip abductor defined in claim 2 wherein said first and second cooperating members include similar shaped and sized disks having a means defining aligned openings, at least one opening having threads found therein for receipt of a fastener, one disk having means defining a second aperture for receipt of a lock pin and the other disk having a lock pin extending therefrom to prevent relative rotation when said members are assembled together.

5. The collapsible hip abductor defined in claim 1 wherein said distal flange portion is generally perpendicular to said mid portion.

6. The collapsible hip abductor defined in claim 1 wherein said wire is approximately 0.187 inch diameter stainless steel.

7. The collapsible hip abductor defined in claim 1 wherein said flexible material is fabricated in sock like fashion to form a fabric tube with two opposing ends, one of said opposing ends being open and the other of said opposing ends being closed.

8. The collapsible hip abductor defined in claim 1 wherein said releasable fastening means is at least one fastening strap secured to said flexible material.

9. The collapsible hip abductor defined in claim 8 wherein each of said straps has two opposing ends, one of said ends has the loop portion of a hook and loop fastening fabric and is attached to said flexible material, the other of said opposing ends is provided with the hook portion of a hook and loop fastening fabric, and the back of said strap is provided with the loop portion of a hook and loop fastening fabric for fastening said one end of said strap to the back of said strap and allowing adjustability of the strap to fit the patient.

10. A collapsible hip abductor device comprising:
first and second support arms for positioning the lower limbs of a patient to properly position the patient's hips and to inhibit improper positioning, each said support arm including a thigh engaging portion having two opposing side edges, a proximal end and a distal end, and a generally triangularly shaped proximal end flange portion extending from said proximal end of said thigh engaging portion to an apex at an angle to said thigh engaging portion of approximately 115°;
attachment means for securing said first and second arms together, comprising a first one of said support arms including a first cooperating attachment member secured to said apex of said proximal end flange of said first support arm;
the second of said support arms including a second cooperating attachment member secured to said apex of said proximal end flange of said second support arm, and said first and second cooperating members being adapted to releasably and directly interconnect for positioning said first and second support arms in a predetermined orientation defining an included angle between said first and second arms of approximately 50°; and
fastening means for releasably fastening each said support arm to an opposing leg of a patient.

11. The collapsible hip abductor defined in claim 10 wherein said first cooperating member has a bottom surface, said second cooperating member has a top surface and said top and bottom surfaces are complementary so that said top surface is butted against said bottom surface to index the relative position of said first and second cooperating members.

12. The collapsible hip abductor defined in claim 11 wherein:

said top surface and said bottom surface are generally planar;
said first cooperating member has a first aperture extending through said first cooperating member, said first aperture being generally perpendicular to said bottom surface;
said first cooperating member has a second aperture extending through said first cooperating member, said second aperture being generally perpendicular to said bottom surface;
said second cooperating member has a third aperture extending through said second cooperating member, said third aperture being aligned with said first aperture and being generally perpendicular to said top surface, at least one of said first and third apertures being threaded;
said second cooperating member has a fourth aperture extending through said second cooperating member, said fourth aperture being aligned with said second aperture and being generally perpendicular to said top surface; and
said attachment means further includes a hand screw for engaging said first and third apertures to screw said first and second cooperating members together; and
said attachment means further includes an indexing pin fastened in one of said second and fourth apertures and projecting therefrom for inserting through the other of said second and fourth apertures to rotationally position said first and second cooperating members relative to each other.

13. The collapsible hip abductor defined in claim 11 wherein said first and second cooperating members include similarly shaped and sized disks having a means defining aligned openings, at least one opening having threads found therein for receipt of a fastener, one disk having means defining a second aperture for receipt of a lock pin and the other disk having a lock pin therefrom extending to prevent relative rotation when said members are assembled together.

14. The collapsible hip abductor defined in claim 10 wherein said distal flange portion is generally perpendicular to said mid portion and the included angle between said proximal flange portion and said mid portion is approximately 115°.

15. The collapsible hip abductor defined in claim 10 wherein said releasable fastening means is at least one fastening strap.

16. The collapsible hip abductor defined in claim 15 wherein each of said straps has two opposing ends, one of said ends has the loop portion of a hook and loop fastening fabric and is attached to said flexible material, the other of said opposing ends is provided with the hook portion of a hook and loop fastening fabric, and the back of said strap is provided with the loop portion of a hook and loop fastening fabric for fastening said one end of said strap to the back of said strap and allowing adjustability of the strap to fit the patient.

* * * * *